US006783989B1

(12) United States Patent
Zakin (10) Patent No.: US 6,783,989 B1
(45) Date of Patent: Aug. 31, 2004

(54) TOXIC SUBSTANCE DETECTION

(75) Inventor: Mitchell R. Zakin, Andover, MA (US)

(73) Assignee: Physical Sciences, Inc., Andover, MA (US)

(*) Notice: Subject to any disclaimer, the term of this patent is extended or adjusted under 35 U.S.C. 154(b) by 476 days.

(21) Appl. No.: 09/590,816

(22) Filed: Jun. 9, 2000

Related U.S. Application Data (60) Provisional application No. 60/138,729, filed on Jun. 11, 1999.

(51) Int. Cl.$^7$ ............................................. G01N 33/00
(52) U.S. Cl. .......................... 436/104; 436/151; 422/90; 422/82.01; 422/82.02
(58) Field of Search ................................ 436/104, 151; 422/90, 82.01, 82.02

(56) References Cited

U.S. PATENT DOCUMENTS

| | | | | |
|---|---|---|---|---|
| 4,657,985 A | * | 4/1987 | Druy et al. | 205/419 |
| 4,765,928 A | | 8/1988 | Thakur | 252/500 |
| 5,145,645 A | | 9/1992 | Zakin et al. | 422/98 |
| 5,227,092 A | | 7/1993 | Han | 252/500 |
| 5,310,507 A | * | 5/1994 | Zakin et al. | 252/500 |
| 5,378,402 A | | 1/1995 | Cross et al. | 252/500 |
| 5,519,147 A | * | 5/1996 | Swager et al. | 528/380 |
| 5,531,932 A | | 7/1996 | Kärnä et al. | 252/518 |
| 5,571,401 A | | 11/1996 | Lewis et al. | 205/787 |
| 5,624,605 A | | 4/1997 | Cao et al. | 252/500 |
| 5,698,089 A | | 12/1997 | Lewis et al. | 205/787 |
| 5,788,833 A | | 8/1998 | Lewis et al. | 205/787 |
| 5,885,650 A | | 3/1999 | Melody et al. | 427/79 |
| 5,891,398 A | | 4/1999 | Lewis et al. | 422/82.02 |
| 5,985,180 A | * | 11/1999 | Beer et al. | 252/500 |
| 6,331,244 B1 | | 12/2001 | Lewis et al. | |

OTHER PUBLICATIONS

Thackery, et al., *J. Phys. Chem.* (1986) 90:6674.
Zakin, M.R. and Marinelli, William J., "Polymer Microsensors for Detection of Chemical Warfare Agents," Presented at the U.S. Army ERDEC Scientific Conference on Chemical and Biological Defense Research (Nov. 1998,).
Zakin, M.R. and Marinelli, William J., "Polymer Microsensors for Detection of Chemical Warfare Agents," Presented at the MASINT Chemical Defense Scientific and Technology Symposium (Jun. 1998,).
McCullough, R.D., et al., "Self–Orienting Head–to–Tail Poly (3–alkylthiophenes): New Insights on Structure–Property Relationships in Conducting Polymers," J. Am. Chem. Soc., 115, 4910–4911 (1993).
Berk, S.C., et al., "Titanocene–Catalyzed Conversion of Enynes to Bicyclic Cyclopentenones," J. Am. Chem. Soc. 115, 4912–4913 (1993).

* cited by examiner

*Primary Examiner*—Jill Warden
*Assistant Examiner*—Monique Cole
(74) *Attorney, Agent, or Firm*—Wolf, Greenfield & Sacks, P.C.

(57) ABSTRACT

Polymeric compositions are provided for use in preparing sensors for the detection of extremely hazardous substances in the environment, such as chemical warfare agents. The polymers are inherently conductive and do not require the use of doping agents to achieve conductivity. The polymers are formulated with appropriate additives which are reactive with the hazardous substances, and are used to prepare sensors. The sensors can be assembled into an array and incorporated into monitoring devices which are highly accurate and relatively inexpensive.

9 Claims, 9 Drawing Sheets

Fig. 1

Regioregular Poly(3-Hexylthiophene)

TOXIC SUBSTANCE DETECTION

CROSS REFERENCE TO RELATED APPLICATIONS

This application claims the benefit of U.S. Provisional Application No. 60/138,729 filed Jun. 11, 1999, the contents of which are incorporated herein by reference in its entirety.

GOVERNMENT RIGHTS

The invention was made with government support under Contract No. F19628-98-C-0065 and F19628-99-C-0014 awarded by the United States Air Force. The government has certain rights in the invention.

BACKGROUND OF THE INVENTION

This invention relates to conductive polymer compositions which are used to detect the presence of toxic substances in the environment. The conductive polymers of this invention are intrinsically conductive polymers which are conductive without the necessity of doping. These conductive polymers can be used in sensors and incorporated in dosimeters to selectively detect the presence of extremely toxic substances in the environment, such as chemical warfare agents.

Accurate selective detection and quantification of toxic substances is generally achievable at relatively high cost. Paper tape sensors coated with a compound which changes color when exposed to a toxic substance can be relatively inexpensive. However, the tape coating layer may respond to a number of discrete substances, making selectivity difficult. Since many substances are present in the environment in trace amounts, the potential for interference or false readings with such devices is significant.

Another category of relatively inexpensive chemical sensors is solid state devices, such as metal oxide films, which display a conductivity change in the presence of certain toxic chemical species, but usually at elevated temperatures. Although adequate for the gross detection of certain chemicals, these metal oxide sensors typically respond to a variety of substances, leading to problems with accuracy and selectivity. In addition, since the devices operate at elevated temperatures, they require a power source for heating and are subject to degradation.

The sensing techniques which have the required sensitivity and selectivity are typically extremely sophisticated, expensive scientific instruments which need to be operated by a skilled technician. For example, mass spectrometers are very sensitive and can achieve the desired selectivity, unless two or more species present in the sample give rise to ions with the same mass to charge ratio. Spectroscopic techniques in principle can achieve the desired selectivity and sensitivity provided that the chemicals do not overlap in terms of their spectroscopic features. However, such instruments typically cost tens of thousands of dollars.

Recent developments in chemical detection involve electronic "noses." These devices are described as being capable of detecting the presence of vapors including methanol, acetone, benzene, and toluene. Such devices are described in U.S. Pat. Nos. 5,698,089; 5,571,401; 5,788,833; and 5,891,398. The devices of these patents relate to chemical sensors, arrays of sensors, and sensor manufacturing techniques. The sensor contains a resistor element which is composed of a nonconductive organic polymer and a conductive material. When the analyte contacts the resistor element, the resistance changes (presumably due to a swelling of the substrate), and this change in resistivity is measured by an electronic signal measuring device. The conductive material can be a conductive polymer, such as doped polyaniline or polypyrrole, and these materials can be incorporated in a portable hand-held electronic device with an LCD read out. The devices described in these patents appear to operate at or near the percolation threshold of the polymer such that the resistivity of the polymer is changed due to the absorption of volatile organic compounds by the polymer matrix.

The use of conductive polymers for fabricating chemical sensors is a relatively recent technological advance. U.S. Pat. Nos. 5,145,645 and 5,310,507 relate to dosimeters for the selective detection of chemical species. The dosimeters include a doped conductive polyaniline which detects the presence of a specific chemical substance by an irreversible change in resistance of the polyaniline. The resistance is measured and displayed in an electronic device connected to the sensor. The individual chemical is identified by correlating the initial polymer resistance with the altered resistance, and comparing this difference with a calibration curve of known chemical entities. Typical chemical entities which may be detected using this approach include hydrazine and ammonia.

Polyaniline is a conductive polymer which has been extensively investigated, both in terms of its properties and potential uses. U.S. Pat. No. 5,624,605 relates to high molecular weight, plasticized, conductive polyaniline compositions. The conductivity of these compositions is provided by adding a functionalized protonic acid to the polyaniline. U.S. Pat. No. 5,378,402 relates to polymeric dopants for enhancing the conductivity of polymers, such as polypyrrole and polyaniline. Sulphonated polystyrene is an example of a negatively charged polymer which is suitable as a dopant. U.S. Pat. No. 5,227,092 is directed to electrically conductive polyaniline block copolymers which are doped using para-toluenesufonic acid as a sulfonated dopant.

U.S. Pat. No. 5,519,147 relates to polythiophene derivatives which contain crown ether moieties covalently bound to the 3 position of adjacent thiophene units. The modified polythiophenes can be used to measure the presence of chemical species, such as metal ions and organic molecules, in a reversible manner. The modified polythiophenes can be used to prepare sensors by coating the polymer onto an insulating substrate, and measuring the difference in conductivity of the polymer in the presence and absence of the species to be detected.

Recent incidents of terrorism around the world have underscored the need for devices for detection of chemical warfare agents ("CW agents") for use by both military and civilian personnel. Despite this need, the sensitive and chemically specific detection of CW agents remains a significant challenge. This is due, in part, to the extreme toxicity of CW agents: the median lethal dose for the nerve agent VX is 7 $\mu$g per kg of body weight for a normal adult, requiring sensitivity levels in the range of parts per billion. Furthermore, to provide maximum effectiveness, CW agent sensors should preferably be used in a badge format that can be worn by each individual to ascertain exposure. This portability requirement places additional constraints on sensor design: the device should be low-cost, have a small form-factor (credit card size), and use very little power (e.g., battery-operated). In addition, it would be useful for a sensor system to have characteristics which are applicable to both military and commercial product markets. Satisfying these demanding requirements necessitates a novel approach to the measurement of low concentrations of CW agents.

It will be readily appreciated that a need exists for a compact dosimeter for the rapid and accurate detection of extremely toxic substances in the environment.

SUMMARY OF THE INVENTION

The present invention features a device and method for detecting the presence of toxic substances in the environment. The device of this invention can incorporate an array of individual sensing elements or sensors which are configured and designed to detect one or more specific toxic substances in the environment. The individual sensors are prepared from conductive polymers which are inherently conductive without the use of a dopant. The conductive polymers are included in a polymeric composition, which also includes at least one additive which reacts with a toxic substance to be detected. The reaction results in a change in a detectable characteristic of the polymeric composition which can be measured and displayed by the detector. Preferably, the change in the detectable characteristic is a change in conductivity of the composition.

Accordingly, in one aspect, inherently conductive polymers are provided for use in sensors for detecting toxic substances in the environment. The inherently or intrinsically conductive polymers do not require the use of dopants to achieve acceptable and measurable levels of conductivity, and, in fact, the use of a doping agent may render the polymers less effective. Polymers which are preferred in this invention include the substituted polythiophenes, such as regioregular poly (3-hexylthiophene) ("rrP3HT"). Regioregular polythiophenes are particularly preferred, and such polymers are described in McCullough et al., *J. Am. Chem. Soc.*, 115, pages 4910–4911 (1993), the pertinent disclosure of which is incorporated herein by reference. The regioregular orientation of the polymer is preferably head-to-tail. The regioregular polymers are semi-crystalline in structure, and the physical distortion of the polymer, such as a torsional distortion or conformational change, results in a change in conductivity. As used herein, and unless otherwise indicated, the term "conductive polymer" is intended to denote such inherently conductive polymers.

In another aspect, this invention includes polymeric compositions which are prepared from the conductive polymers and at least one additive. The additive is a substance which is permanently or irreversibly reactive with the CW agent to be detected. Such additives can be physically incorporated into the polymer by blending, copolymerized with the conductive polymer, or reacted with a pendant group of the polymer. Preferably, the additives are antidotes for the CW agents, such as syn-2-pyridine aldoxime ("oxime") and 2-pralidoxime chloride ("2-PAM"). The additives interact with the CW agent, and cause distortion of the polymer, resulting in a change in conductivity.

In a further aspect of this invention, the polymeric composition can be used to prepare sensors. In addition to the polymeric composition, the sensors include a means for measuring a change in the detectable characteristic of the polymer in the presence of a toxic substance. The change in detectable characteristic is preferably a change in the conductivity or resistivity of the composition. However, other detectable changes which can be measured include changes in optical properties, changes in mass, and changes in capacitance or impedance. These changes can be measured using standard devices and instrumentation. For instance, surface acoustic wave devices or piezoelectric devices, such as quartz microbalances, for measuring the change of mass, UV, visible light or passive IR absorption for measuring a change in optical properties, comparators for electrical resistance measurement, and devices for measuring the reaction products resulting from the reaction of the CW agent and the additive. These measurement means are not intended to be exclusive, and more than one type of measurement can be made in response to one or more toxic substances.

In one particularly preferred embodiment of this aspect of the invention, the detectable change is a change in the resistivity of the sensor, and the polymeric composition is applied as a film to a suitable substrate material. In this embodiment, a thin film of the polymeric composition is applied to a suitable substrate material, preferably a non-conductive substrate, such as glass, a ceramic, or a non-conductive polymer. The sensor can incorporate electrical contact points or electrodes for connecting the sensor to a voltage or current source, or to other sensors to form an array of two or more of such sensors. The polymeric composition used to prepare an individual sensor can also include more than one additive component, with each additive being reactive with a single or different CW agent, provided that the CW agents are all part of a single class of such agents such that an individual sensor can respond to a variety of CW agents within a single class. The sensor array can include a plurality of individual sensors which may be responsive to a variety of CW agents in multiple chemical classes. Preferably, the sensor array comprises at least two individual sensors and is capable of responding to three classes of CW agents, i.e. the G-class of agents, such as GA, GB and GD; the H-class of agents, such as HD; and the V class of agents; such as VX. These agents typically have sufficient volatility to be detected as airborne toxins. The toxic substances of this invention can include substances other than CW agents, such as pesticides. This capability provides broad versatility to the detection device. The sensor array can also include individual sensors prepared from a diversity of conductive polymers, including conductive polymers which are not inherently conductive and may require the use of a dopant.

Another aspect of this invention is the use of a mathematical formula to correlate the response of the sensor to the concentration or dose of a particular CW agent, or group of CW agents, in the environment. Such mathematical models can be constructed for both reversible responses, which are concentration dependent, and irreversible responses, which are dosage dependent. In general, the responses to CW agents are irreversible due to the highly specific binding of the agent and the reactive additive.

In an additional aspect of the invention, a detection device is provided for displaying information indicative of a lethal dose of a CW agent in the environment. The device is preferably a dosimeter containing a sensor array, means for converting the measurable change in the detectable characteristic into a signal, means for comparing the signal with the response of the sensor array to a known or predetermined toxic substance, and means for displaying information on the concentration, dose or toxicity of the CW agent. The dosimeter can also include a microprocessor, data storage, and an alarm. The circuitry is compact and can be designed to fit into a credit-card sized monitor, which can be worn as a badge by the user.

DETAILED DESCRIPTION

Various specific embodiments of this invention will now be described.

The polymeric sensors of the present invention are designed to couple the chemistry of a class of CW agents to the electronic conduction pathway of the polymer to provide a measurable change in polymer resistance indicative of the chemical interaction. This change in resistance can then be directly and accurately related to CW agent exposure dose or concentration. The mathematical relationship between exposure dose and the change in resistance constitutes the calibration function for the polymeric sensor device. The calibration parameters depend strongly on the particular polymer-agent combination, and have been found to exhibit a predictable dependence on environmental conditions, such as temperature and relative humidity ("RH"). Once the full calibration of the sensor system against concentration, temperature, and RH is established, the measurement of polymer resistance yields a precise and accurate quantification of CW agent dose and/or concentration.

One target class of CW agents which are readily detectable using the sensors of this invention are the organophosphate inhibitors of the enzyme cholinesterase (G- and V-class chemical warfare agents) and vesicants (H-class agents). From a toxicological standpoint, both cholinesterase inhibition and vesicant action are relatively simple toxicological endpoints.

Polymers which are "electroactive" are essentially plastics that conduct electricity. Chemical vapors interact with the polymer backbone, or a chemically reactive additive incorporated into the polymer, to produce a change (increase or decrease) in the electrical resistance of the polymer, which enables the polymer to function as a chemical sensor. A measurement in the change in polymer resistance provides an accurate quantification of the dose or concentration of a particular CW agent.

Electroactive polymers exhibit a key common feature: a high degree of conjugation, i.e., alternating single and double bonds. Conjugation permits efficient delocalization and motion of charge along the polymer chains, giving rise to high electrical conductivity. However, since the conjugation length of these materials is small (typically~7 repeat units), charges must "hop" between chains; the bulk conductivity is thus determined by this relatively inefficient interchain hopping process. This latter property restricts the conductivity of electroactive polymers to the sub-metallic regime.

The response of electroactive polymers to chemical species can be either concentration or total dose sensitive. The response of concentration-sensitive polymers to chemical species is reversible; the polymer resistance returns to its starting (baseline) value when the polymer is removed from the environment containing the target species. In contrast, the response of total dose sensitive polymers is permanent; the resistance does not change after the polymer is removed from the measurement environment. The response characteristics for concentration and dosimetric sensors are described by Eq. 1 below:

$$\frac{R}{R_0} = \frac{R_\infty/R_0}{1 + \left(\frac{R_\infty}{R_0} - 1\right)e^{-k_d d}} \quad \text{Eq. (1)}$$

wherein
R=instantaneous resistance
$R_o$=initial resistance
$R_{2S}$=saturation resistance (d→∞)
$k_d$=sensitivity (mg-min/m$^3$)$^{-1}$
d=exposure dose (mg-min/m$^3$)

Figure 1:
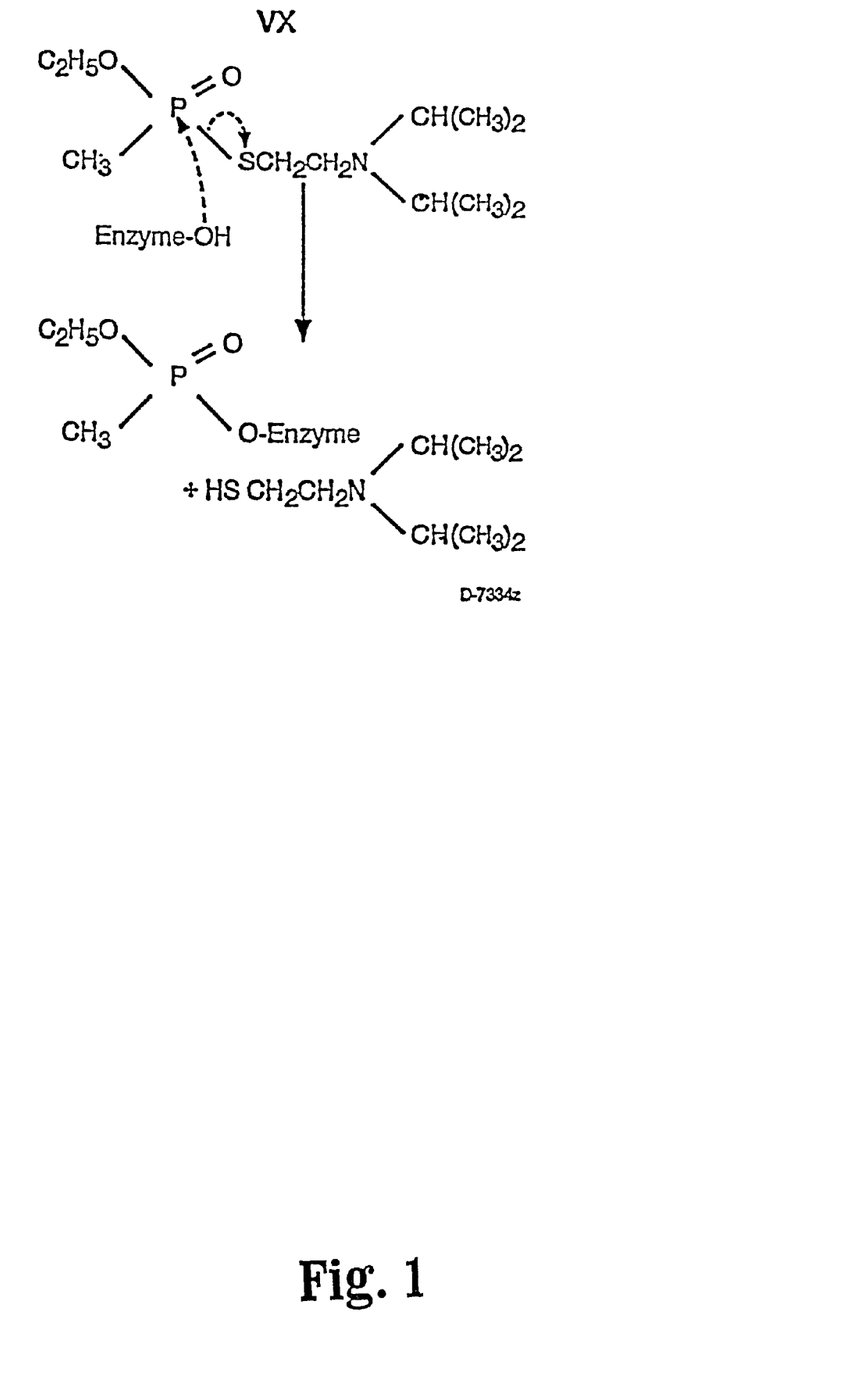
FIG. 1 illustrates the chemical reaction of VX with cholinesterase.

G- and V-class chemical warfare agents are organophosphorous compounds which inhibit cholinesterase by direct nucleophilic reaction, preventing the enzyme from binding the neurotransmitter acetylcholine in the nerve synapse. The build-up of acetylcholine rapidly leads to progressive loss of muscle control and function, and ultimately, to death. The common G agents include GA, GB (sarin), and GD, while the V agents are typified by VX. The structure of the most deadly CW agent, VX, and the reaction of VX with cholinesterase, are shown in FIG. 1.

G and V agents have a central phosphorous atom bound to four chemical groups: an oxygen (or sulfur) atom, two alkyl or alkoxy groups, and a leaving group (e.g., the bulky S-containing group on VX). The weakest bond in the compound is the link between the P and the leaving group. Thus, the key reaction is the facile cleavage of that bond, denoted the P—X bond, by strong nucleophiles including the cholinesterase enzyme. As illustrated in FIG. 1, the nucleophilic attack on the electrophilic P atom results in the formation of a covalent bond between the nucleophile and the P atom and the concomitant expulsion of the leaving group.

The H-class CW agents are typified by sulfur mustard, HD, which is a chlorosulfide of structure S(CH$_2$CH$_2$Cl)$_2$. HD acts to alkylate the nitrogen containing components of proteins and DNA in-vivo via direct nucleophilic reaction with the Cl end-groups.

Figure 2:
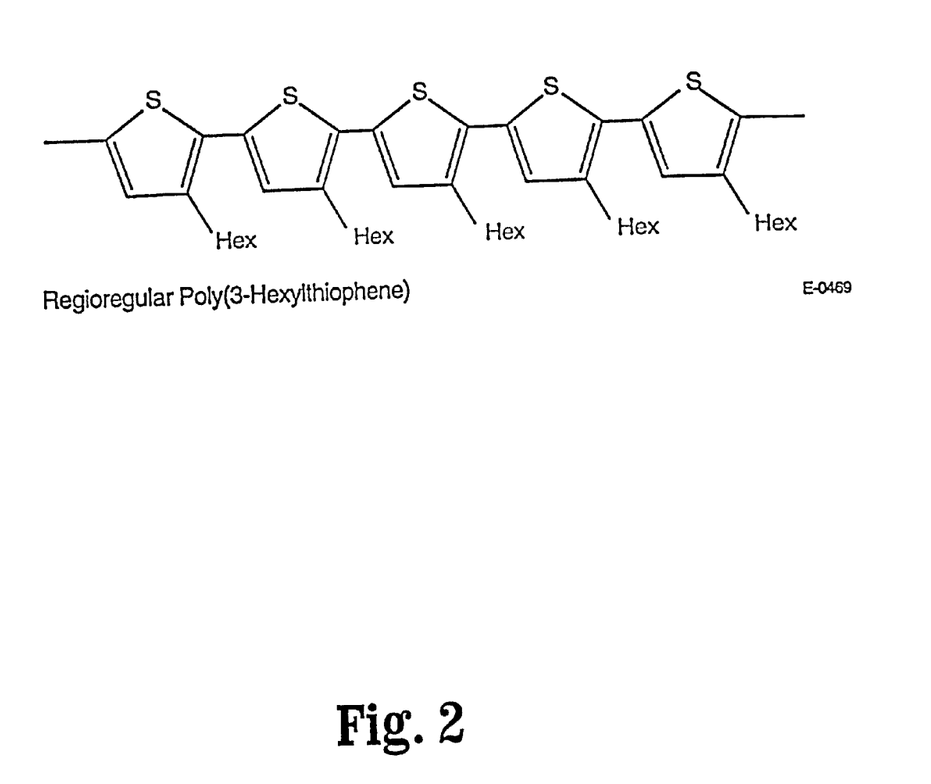
FIG. 2 illustrates the structure of regioregular poly (3-hexylthiophene).

The electroactive or conductive polymers encompassed by this invention include the regioregular class of polymers. Such polymers are described in McCullough et al., *J. Am. Chem. Soc.*, 115, pages 4910–4911 (1993). A typical example of a regioregular polymer which is operable in this invention is regioregular poly(3-hexylthiophene) ("rrP3HT"). The structure of this polymer is shown in FIG. 2.

The regioregular polymers, such as the rrP3HT material, are intrinsically conductive without doping, and thus are extremely stable under a broad range of operational conditions. The lack of doping renders the regioregular polymers particularly amenable to the incorporation of reactive additives. Reaction of CW agents with the reactive additives in rrP3HT produces a torsional distortion of the polymer backbone, giving rise to a change in resistance. The regioregular polymers are highly environmentally stable, and are easily processed into thin film form, required for fabrication of sensor elements, from common solvents.

Table 1 contains a listing of electroactive polymers and reactive additives which are useful in the practice of this invention. These additives include the oxime compounds 2-pralidoxime chloride (2-PAM) and syn-2-pyridine aldoxime (oxime), which are known effective antidotes for G and V agent poisoning.

TABLE 1

| Agent Class | Polymer | Additive |
| --- | --- | --- |
| G, V, H | rrP3HT | syn-2-pyridine aldoxime (oxime) |
| G, V | rrP3HT | 4-dimethylaminopyridine (DMAP) |
| V | rrP3HT | 2-pralidoxime chloride (2-PAM) |

Regioregular polythiophenes are sufficiently hydrophobic to produce strong adsorption of the G, V, and H agents, and thus promote interaction between the agents and the reactive additives. These polymers when modified with reactive additives, demonstrate rapid, ultrasensitive, and high dose capacity detection of CW agent exposure doses for the three agent classes.

As shown in more detail in the accompanying examples, the polymer formulations of this invention can be used for real-time detection of G, V, and H-class chemical warfare agents at sub-miosis level doses. This is accomplished by using the formulations to fabricate sensors, and integrating the sensors into a readout device.

Sensors can be prepared by coating an appropriate substrate with the polymer formulations of the invention. The sensor can have electrodes or electrical contact points embedded in it for establishing a voltage across the sensor, and measuring the change in resistance in the presence and absence of a chemical agent. The substrate is preferably a non-conducting material, such as glass, a non-conductive polymer, a ceramic, and the like. A preferred plastic substrate material is Mylar, a flexible and rugged plastic material which exhibits excellent adherence to the electroactive polymer sensor materials. Furthermore, incorporation of metallic electrodes (gold, aluminum) into Mylar is readily and inexpensively achieved using standard photolithographic techniques.

The polymer film thickness, the initial polymer resistance, the reactive additive content in the polymer, and the material hydrophobicity can be adjusted to obtain optimal performance of the sensor. Each of these parameters can influence the sensitivity and response characteristics of the polymeric composite materials. The film thickness, which contributes to sensitivity and response time (thinner films are more sensitive and exhibit faster response), can be varied by adjusting the concentration of polymer in the coating solution. The initial polymer resistance, which is directly proportional to sensitivity, can be varied by adjusting either the polymer chemical structure or the thin film deposition process. Optimization of the reactive additive content can be achieved, for example, by simply adjusting the additive concentration in the polymer processing solution.

If it is desired to ensure that no false positives are detected, the species-specificity of the polymer sensors must be significant. Sufficient specificity can often be partially achieved by optimization of the reactivity and other characteristics of the electroactive polymer sensor materials as described above, since this process enhances the interaction with CW agents while minimizing interaction with potential interferents, such as solvents and organophosphorous pesticides. To obtain further specificity for demanding applications, arrays of polymer sensors, each with a distinct response to agents and interferents, can be constructed. The composite response of the array provides a unique "fingerprint" for each agent, and can be analyzed by principal component analysis or a neural network to provide the agent identity as well as concentration.

Figure 9:
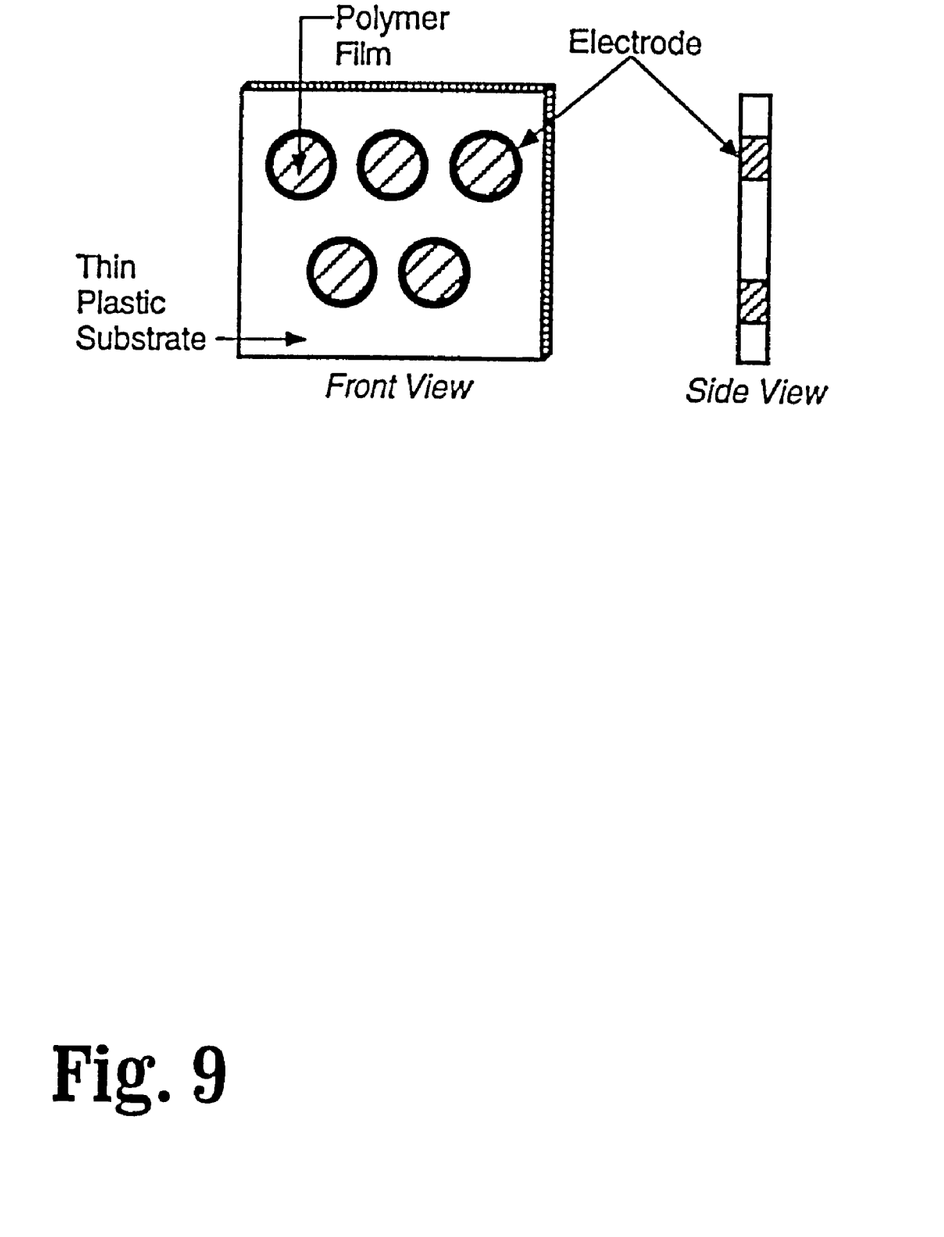
FIG. 9 is a schematic drawing of a sensor array.

Sensor arrays are constructed from the two or more individual sensors. A typical array is shown in FIG. 9. The array can consist of five individual polymer thin-film sensors, each specific for a single target species class, coated onto a thin plastic carrier substrate. The substrate can have integral electrodes (two for each sensor) in order to make electrical contact with each film and connect the films to the resistance measuring circuitry. The polymer films are coated directly onto the electrodes residing on the outer exposed surface of the substrate. If required, an inexpensive microporous membrane, such as those produced by the Pall Corporation, can be placed over the sensor assembly. Such membranes seal out liquids and heavy particulates while allowing unrestricted flow of air and gases. The shape and size of the carrier substrate, as well as the spatial arrangement of the sensor electrodes on the substrate surface, are chosen to facilitate the deposition of thin polymer films.

Typical film thicknesses are on the order of 1000 Å, so very little polymer material, on the order of 0.1 to 1 $\mu$g, is deposited to form a sensor film. Useful deposition techniques include spray-coating, spin-coating, dip-coating, ink-jet printing and painting.

The key elements of the detector or monitor are the microsensor array and a readout device. A typical device consists of an array of five polymer sensors and a small, low-cost readout device. Each sensor in the array is provides a distinct response to the three classes of chemical warfare agents—G, V, and H.

The monitor should be capable of providing rapid, real-time indication of CW agent exposure dose in an operational environment containing multiple toxic species whose identities may not be known. The device should also be capable of continuously and accurately monitoring CW agent cumulative dose at sub-miosis levels over extended period of time, and storing the exposure history for future download. The monitor is preferably passive and non-intrusive, roughly the size of a credit card, and disposable.

An array of polymer sensor elements, whose composite response provides both quantification and species-specific identification of CW agents, is incorporated into the monitor. The sensing elements can be replaceable and disposable.

Figure 10:
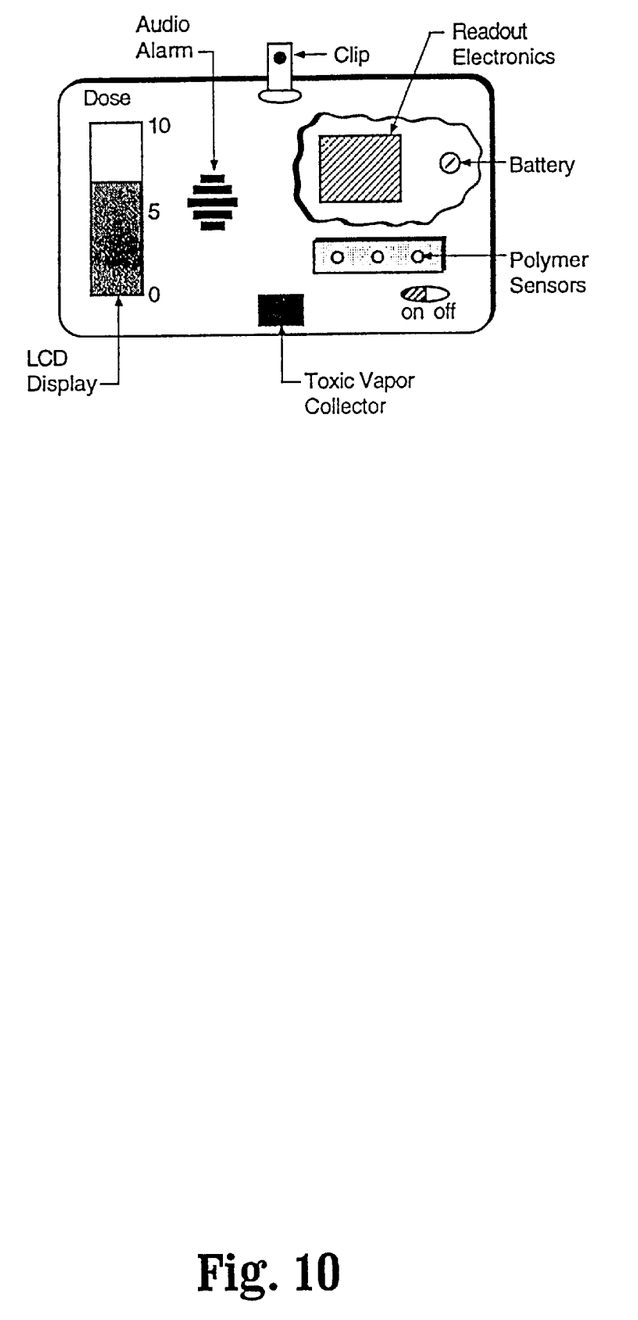
FIG. 10 is a schematic diagram of the detector or monitor.

A schematic diagram of one monitor design is shown in FIG. 10. The form factor of the monitor is roughly that of a credit card, but slightly thicker (5 mm) to accommodate the size of the various internal components. An array of five polymer sensors is integrated into a single carrier substrate, and inserted into a mating receptacle on the front of the device. Each polymer sensor can be designed to provide a distinct response to the three classes of chemical agent species: G, V, and H. The integrated sensor/carrier substrate assembly can be disposable, and thus the receptacle will be designed for facile and rapid interchange of the sensor array. The resistance of the polymer sensors can be rapidly measured in a multiplexed fashion by dedicated circuitry. The resistance measurements can be converted to total exposure dose by an on-board microprocessor via a predetermined calibration function. Software algorithms residing on the microprocessor can control all device operational functions, as well as perform the resistance-to-dose conversions. The device can store dose exposure history and provide means for downloading this history to a personal computer. The device can provide a real-time indication (on an LCD display) of total exposure dose and the total cumulative integrated exposure dose from a user-determined starting point. Audio and/or visual alarms can be employed to indicate when a pre-set exposure dose has been exceeded. The device can be powered by a small battery, and can feature a clip or other attachment means for securing the device to a pocket or belt.

Figure 11:
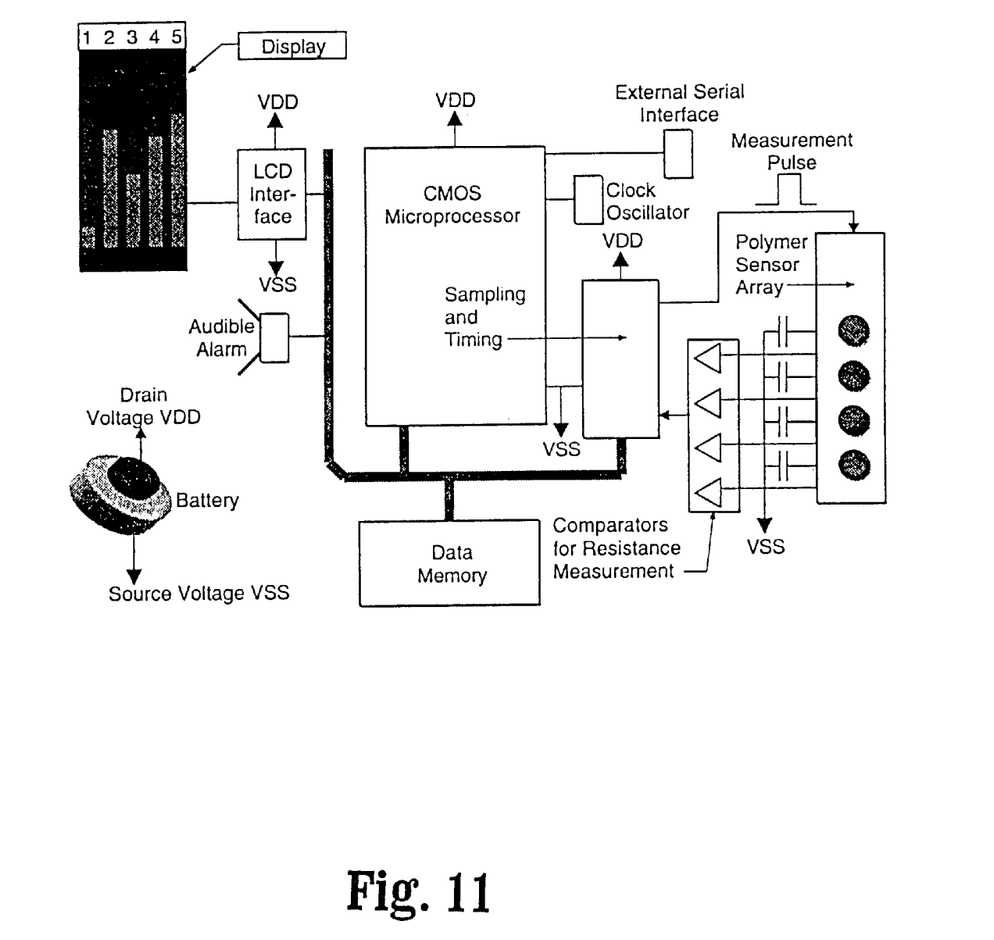
FIG. 11 is a block diagram of the monitor.

A detailed conceptual design of one embodiment of the monitor is shown in FIG. 11. This design translates the device concept presented above into a series of components to perform the required individual unit operations and functions of the monitor. The specification of the components of the resistance monitoring circuitry will depend upon several characteristics of the polymeric sensor elements, including initial resistance, resistance dynamic range, and response time.

The sensor resistance measurements are performed by attaching one of the two terminals of each polymer sensor to a capacitor and applying a voltage to the second terminal. The sensor resistance is proportional to the time required for the voltage on the capacitor to reach a predetermined level (e.g., 1.0 V). This technique provides rapid multiplexed measurement of the five polymer films in the sensor array. The measured data is stored in a software register on the microprocessor for conversion to dose. A small liquid crystal (dot graphics) display (Epson Seiko) can be used as the output device. During normal operation a simple "thermometer" graphic is periodically updated to display total exposure dose over a preselected time interval, in real-time, for the three chemical classes. This display is alternated with a graphic indicating total integrated exposure dose. Specific diagnostic messages (e.g., "low battery," "extreme temperature," "sensor not operational," etc.) can be displayed as appropriate.

A CMOS static microprocessor can be employed in the monitor. Examples of commercially available high-volume devices include the Intel 8xC51, Motorola 68HCxx, and Microchip PIC16C6xx series.

Custom software algorithms for control of the various monitor operations can be developed and written in the programming language C or C++. Efficient Kalman filter-based algorithms can be used for data processing. Such algorithms have minimal memory requirements and eliminate the need for floating point or high precision integer math, thus resulting in lower microprocessor power consumption.

The monitor has a variety of applications in the military and commercially significant markets in medical, environmental, and industrial chemical detection. Particular applications include high-throughput screening of pharmaceutical candidates, personal protection, breath analysis for rapid medical diagnostics, monitoring of hazardous waste sites during remediation activities, regulatory compliance, and the rapid and inexpensive assessment of the toxicity of unknown or newly synthesized compounds.

The following examples are intended to illustrate the various aspects of the invention without limiting it thereby. As will be appreciated by those skilled in the art, various changes can be made to the procedures, methods and materials employed in the examples without departing from the spirit and scope of the present invention. The present invention is intended to encompass all such variations.

EXAMPLE 1

Preparation of Polymer Sensor

Chemical sensors are prepared by depositing films of the polymers of the invention onto supporting substrates. The substrate consisted of a small glass or Mylar slide (1 in.×0.5 in., or smaller) incorporating a set of gold interdigitated electrodes on its surface. These electrodes provide precise electrical contact to the polymer sensing film. Large gold contact pads on the substrate surface provide simple connection to a resistance monitoring device, such as a digital multimeter. The polymer film is deposited directly onto the electrodes by a variety of means including spray-, spin-, and dip-coating or ink jet printing of a dilute solution of the polymer dissolved in an appropriate solvent. For example, spin-coating is performed by applying a 50 $\mu$l drop of polymer solution directly onto the electrodes using a microdispenser, and then the substrate is spun at 3000 rpm for 30 seconds using a commercial photoresist spinner (Headway Systems) to form the film. Typical film thickness is on the order of $10^3$ Å.

EXAMPLE 2

Testing of Sensor

A custom-built system was utilized to measure sensor resistance in real-time upon exposure to CW agents. This system consisted of a Keithley digital multimeter equipped with a 10-channel multiplexer and coupled to a notebook computer containing a PCMCIA-based GPIB board. Custom software was written in LabView to control all measurement functions including data sampling rate. The system is capable of measuring the resistance of up to 10 polymeric sensors at an accuracy of ±0.05% at data sampling rates exceeding 4 Hz. The measurement system was utilized for both laboratory-based sensor development, and sensor testing against live CW agents. The live CW agents evaluated included G, V, and H agents.

Representative conditions for testing the polymeric sensors against live CW agents are summarized in Table 2. These conditions were chosen to examine the low-dose behavior of the sensors. The sensor materials had previously been screened at higher concentrations to establish the approximate dose capacity (maximum dose before saturation) of the sensors. Examination of the behavior of the polymer sensors in the low-dose region is important to establish the sensitivity of the devices at "low hazard" levels. These levels correspond to doses at or below the miosis level, the key indicator of low-dose exposure to CW agents. Miosis is constriction of the pupils due to loss of the accommodation ability of the ciliary muscles in the eye, leading to impaired vision.

The basic experimental procedure consisted of placing the sensors (10 at a time) into a 5-liter glass vessel into which a dilute agent stream was introduced at a flow rate of 5 l/minute. The diluent was humidified air. The vessel was passivated with each CW agent prior to introduction of the sensors. The sensors were electrically connected to the automated resistance measurement system for real-time measurement of the change in polymer resistance upon exposure to the agent. All resistance measurements were performed at a data sampling rate of 4 Hz to ensure sufficient dose resolution at very low exposure doses.

TABLE 2

| Agent | Concentration (mg/m$^3$) | Temperature (° C.) | Relative Humidity (%) |
| --- | --- | --- | --- |
| GD | 0.2 | 20 | 5, 50 |
| VX | 0.002 to 0.02 | 20 | 5, 50, 90 |
| HD | 0.6 | 20 | 50 |

The measured change in polymer resistance was used to establish the mode of interaction of the polymer with each CW agent (reversible or dosimetric) and to determine the polymer sensitivity $k_d$ (dosimetric) or $K_{eq}$ (reversible). In all cases the interaction was found to be dosimetric.

EXAMPLE 3

Polymer Response Model to Determine $k_d$

Figure 3:
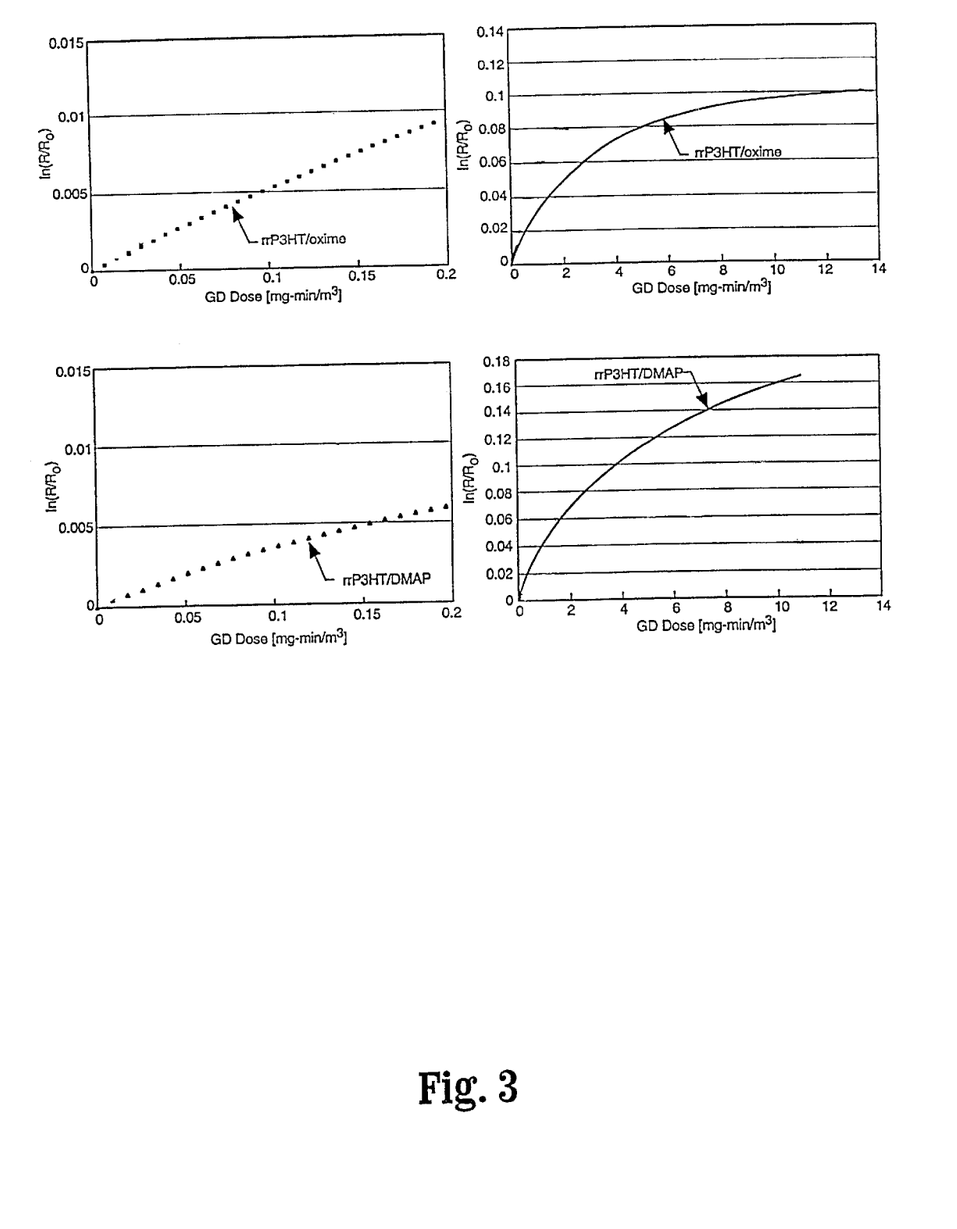
FIG. 3 is a graph of the polymer sensor response for low and high doses of GD.
Figure 4:
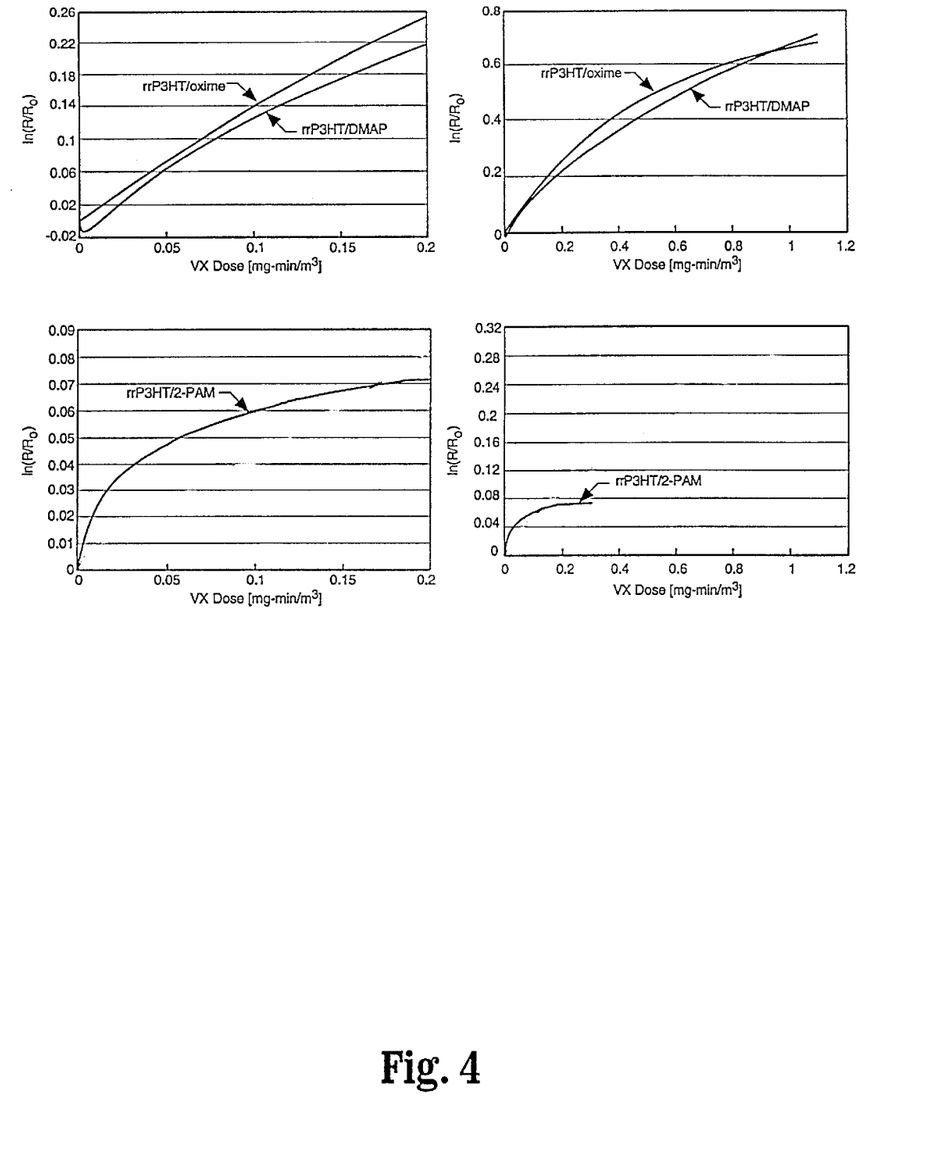
FIG. 4 is a graph of the polymer sensor response for low and high doses of VX.
Figure 5:
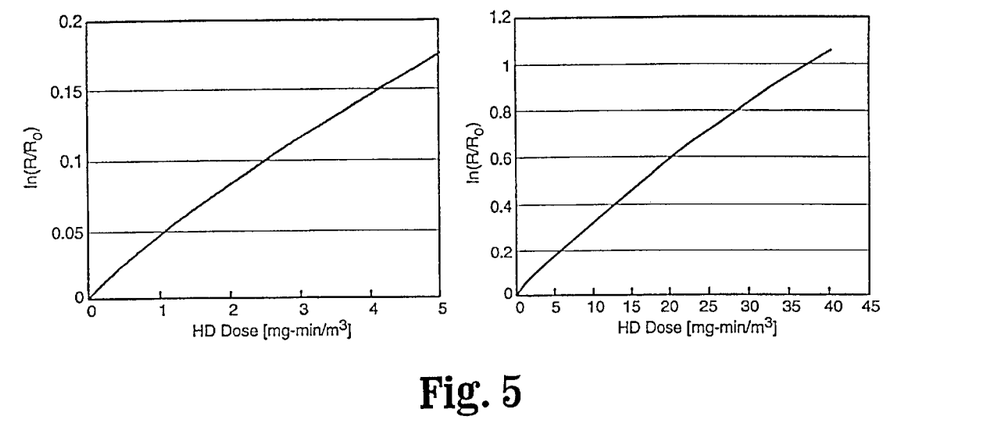
FIG. 5 is a graph of the polymer sensor response for low and high doses of HD

Response curves for the various polymeric sensor materials (listed in Table 1) to G, V, and H agents, obtained by averaging the responses of multiple replicate polymeric sensors, are displayed in FIGS. 3 through 5, respectively. In these Figures, the polymer response $R/R_o$ is plotted on a semilogarithmic scale against CW agent exposure dose. Separate curves are plotted for the low dose and higher dose regimes. All data were obtained at 20° C. and 50% RH. The higher dose curves correspond to an exposure dose ranging from zero to the maximum agent exposure dose delivered in the real-time surety experiments. The low dose curves correspond to an exposure dose ranging from zero to approximately twice the miosis level dose (for HD, this dose is twice the "low hazard level" dose), and are a subset of the total exposure data. FIGS. 3 through 5 reveal a strong change in polymer resistance for these very low agent doses, indicating the high level of sensitivity towards the three classes of CW agents. Note also the deviation from linearity (i.e., the expression of Eq. 1 in the limit $k_d d<<1$) for several of the polymer formulations, particularly at higher doses. This indicates that the low-dose limit for $R/R_o$ has been exceeded for these formulations. An accurate determination of the polymer sensitivity $k_d$ thus requires use of the mathematical model of Eq. 1 for the polymer response which accounts for the full exposure dose behavior (low dose to saturation). Saturation occurs when the polymer dose capacity has been exceeded, i.e., further exposure of the material to agent produces no additional change in resistance.

Figure 6:
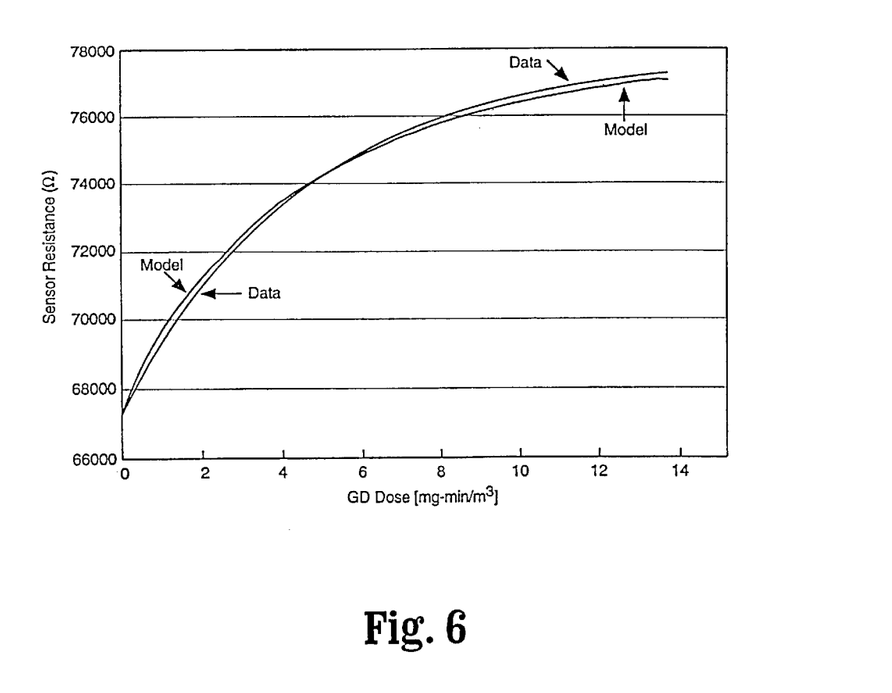
FIG. 6 is a graph representing the fit of polymer response function to experimental data for the detection of GD with rrP3HT/oxime.

A fit of Eq. (1) to the curves in FIGS. 3 through 5 directly yields $k_d$. A representative example of such a fit is given in FIG. 6, which compares the best model fit to experimental data for detection of GD with a rrP3HT sensor incorporating an oxime additive. Eq. (1) provides an accurate representation of the experimental data over a wide dynamic range.

Figure 7:
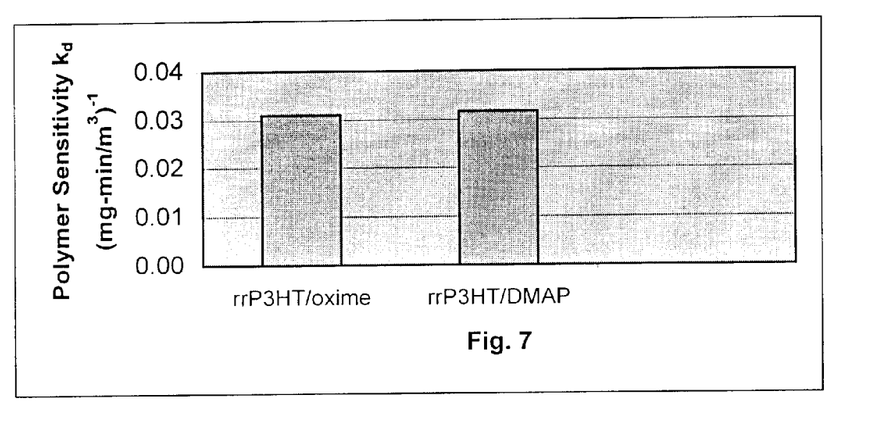
FIG. 7 is a bar graph showing polymer sensitivity toward GD.
Figure 8:
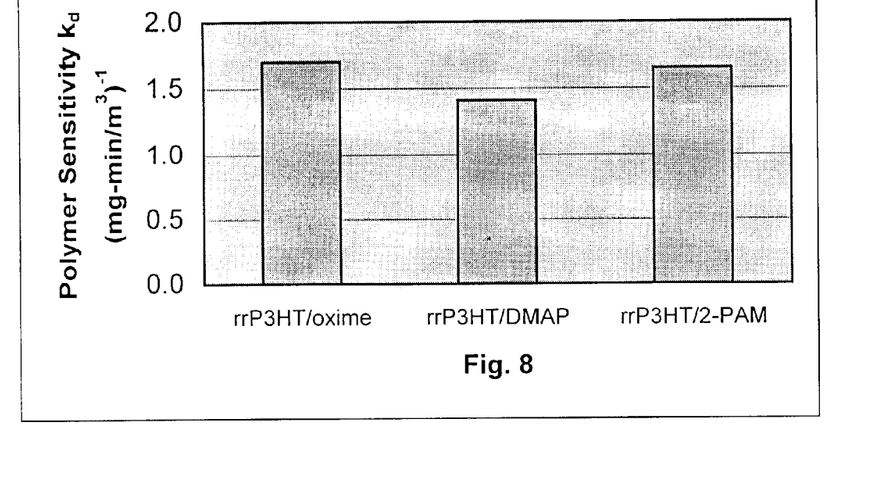
FIG. 8 is a bar graph showing polymer sensitivity toward VX.

The polymer sensitivities $k_d$ for G and V agents, obtained by the above analysis, are displayed in bar-chart form in FIGS. 7 and 8, respectively. The corresponding value of $k_d$ for HD is 0.010 (mg-min/m³)$^{-1}$. Note that the various polymer formulations are significantly more sensitive towards VX than GD or HD (VX>GD>HD); this is an important result since the desired detection levels for VX are significantly lower than for G or H agents.

The polymer sensitivities $k_d$ can be used to derive the minimum detectable exposure dose $d_{min}$ for the three classes of agents, based on the accuracy to which the sensor resistance can be measured in practice. The minimum detectable dose can be expressed as:

$$d_{min} = \Delta R_{meas}/(k_d \Delta R e^{k_d d}) \quad \text{Eq. (2)}$$

where $\Delta R_{meas}$ is the accuracy to which $\Delta R$ can be measured. With the conservative assumption that $\Delta R$ can be measured to within 1 part in $10^3$, Equation (2) reduces to:

$$d_{min} = e^{k_d d}/1000 k_d \quad \text{Eq. (3)}$$

Equations (2) and (3) correspond to a measurement signal-to-noise (S/N) ratio of unity. At a more conservative S/N of 5, $d_{min}$ is a factor of 5 higher. The calculated $d_{min}$ ranges for S/N=5 are displayed in Table 3 for the various agents. These values are below the miosis level doses ("low dose hazard" level dose for HD) for the agents. All $d_{min}$ values are calculated using the miosis level or "low dose hazard" level for d in Eq. (3); $d_{min}$ varies only mildly with d at low dose.

TABLE 3

| Agent | $d_{min}$ (mg-min/m³) | Miosis Level (mg-min/m³) |
|---|---|---|
| GD | 0.02 to 0.03 | 0.2 |
| VX | 0.001 to 0.01 | 0.09 |
| HD | 0.50 | 2.5 to 25 (low dose hazard) |

The above data demonstrates the robust detection of G, V, and H agents below the miosis (or low dose hazard) levels using electroactive polymer sensors.

As mentioned above, the polymer formulations function as dosimetric sensors, namely that the change in sensor resistance upon exposure to agents is permanent. This indicates that each sensor material has a finite exposure dose capacity $d_{max}$ after which the sensor becomes saturated, i.e., further exposure to agent produces no further change in sensor resistance. Table 4 lists approximate dose capacity ranges for the polymeric sensors with respect to detection of the various CW agents. In most cases the exposure doses examined were not sufficient to determine the actual value of $d_{max}$; however, it is apparent from Table 4 that the polymeric sensors have significant dose capacity, in some cases exceeding $LD_{50}$, the median human lethal dose.

TABLE 4

| Agent | $d_{max}$ (mg-min/m³) | $LD_{50}$ (mg-min/m³) |
|---|---|---|
| GD | ≧10 (rrP3HT) | 70 |
| VX | >2 (rrP3HT) | 30 |
| HD | >40 (rrP3HT) | 1500 |

What is claimed is:

1. A polymeric composition in combination with a sensor to detect the presence of toxic substances in the environment comprising an undoped intrinsically conductive polymer and at least one additive, said additive being capable of irreversibly reacting with a toxic substance to be detected and changing a detectable characteristic of the composition, wherein the at least one additive is selected from the group consisting of syn-2-pyridine aldoxime, 3-trifluoromethyl-1-benzamidoxime, 4-dimethylaminopyridine, and 2-pralidoxime chloride.

2. A polymeric composition in combination with a sensor to detect the presence of toxic substances in the environment comprising an undoped intrinsically conductive polymer and at least one additive, said additive being capable of irreversibly reacting with a toxic substance to be detected and changing a detectable characteristic of the composition, wherein the toxic substance is a chemical warfare agent, a chemical warfare agent precursor, or a chemical warfare agent decomposition product.

3. The polymeric composition of claim 2 wherein the additive is an antidote to a chemical warfare agent.

4. The polymeric composition of claim 2 wherein the chemical warfare agent is selected from the group consisting of VX, GA, GB, GD and HD.

5. A polymeric composition in combination with a sensor to detect the presence of toxic substances in the environment comprising an undoped intrinsically conductive polymer and at least one additive, said additive being capable of irreversibly reacting with a toxic substance to be detected and changing a detectable characteristic of the composition, wherein the toxic substance is a pesticide.

6. A polymeric composition in combination with a sensor to detect the presence of toxic substances in the environment comprising an undoped intrinsically conductive polymer and at least one additive, said additive being capable of irreversibly reacting with a toxic substance to be detected and changing a detectable characteristic of the composition, wherein the toxic substance is an organophosphate cholinesterase inhibitor.

7. A sensor for detecting the presence of a toxic substance comprising:

a polymeric composition in combination with a sensor to detect the presence of toxic substances in the environment comprising an undoped intrinsically conductive polymer and at least one additive, said additive being capable of irreversibly reacting with a toxic substance to be detected and changing a detectable characteristic of the composition, and means for measuring the change in the detectable characteristic of the polymeric composition upon exposure to the toxic substance wherein the toxic substance is selected from the group consisting of chemical warfare agents and pesticides.

8. The senor of claim 7 wherein the toxic substance is a chemical warfare agent selected from the group consisting of VX, GA, GB, GD and HD.

9. A method for detecting the presence of a specific toxic substance in the environment comprising:

forming a sensor from an undoped intrinsically conductive polymer & at least one additive composition which is capable of reacting with a specific toxic substance to be detected, exposing the sensor to an environment which may contain a toxic substance, measuring the change in a detectable characteristic of the sensor in the presence of the toxic substance, determining whether the change in the detectable characteristic is within a predetermined range for the toxic dose of the specific toxic substance, wherein the toxic substance is a chemical warfare agent.

* * * * *